United States Patent [19]

Nakano et al.

[11] Patent Number: 5,189,187

[45] Date of Patent: Feb. 23, 1993

[54] DITERPENE COMPOUND AND PROCESS FOR PRODUCING THE SAME

[75] Inventors: Hirofumi Nakano, Tokyo; Shozo Kawada, Yamaguchi; Yoichi Uosaki; Yutaka Saito, both of Tokyo; Katsushige Gomi, Shizuoka; Toshiaki Iwazaki, Shizuoka, all of Japan

[73] Assignee: Kyowa Hakko Kogyo Co., Ltd., Tokyo, Japan

[21] Appl. No.: 903,476

[22] Filed: Jun. 24, 1992

Related U.S. Application Data

[62] Division of Ser. No. 767,819, Sep. 30, 1991.

[30] Foreign Application Priority Data

May 10, 1990 [JP] Japan ................................. 2-267840

[51] Int. Cl.$^5$ ............................................ C07D 303/32
[52] U.S. Cl. ..................................... 549/548; 549/458; 549/488; 549/361
[58] Field of Search ............... 549/548, 458, 488, 361

[56] References Cited

U.S. PATENT DOCUMENTS 4,576,961 3/1986 Lorck et al. ..................... 514/462

FOREIGN PATENT DOCUMENTS 205981 12/1986 European Pat. Off. ............ 514/462

OTHER PUBLICATIONS

Bailey et al., Tetrahedron, 2(7), pp. 495–509 (1991).
Kawada et al., Cancer Res. 51(11), pp. 2922–2955 (1991).
Bailey et al., Tetra Lett., 31(31) pp. 4509–4512 (1990).
Isshiki et al., J. Antibiot, vol. 38(12), pp. 1817–1821 (1985).

*Primary Examiner*—James H. Reamer
*Attorney, Agent, or Firm*—Nixon & Vanderhye

[57] ABSTRACT

A clerodane-type diterpene derivative, which has antibacterial and antitumor activities, as well as chemically equivalent tautomers thereof and a process for producing said derivative using a microorganism belonging to the genus Streptomyces.

1 Claim, 2 Drawing Sheets

DITERPENE COMPOUND AND PROCESS FOR PRODUCING THE SAME

This is a continuation of application Ser. No. 07/767,819, filed Sep. 30, 1991.

FIELD OF THE INVENTION

This invention relates to UCT-4B, which is a clerodane-type diterpene having antitumor and antibacterial activities, and a process for producing a compound having a clerodane-type diterpene structure using a microorganism belonging to the genus Streptomyces.

BACKGROUND OF THE INVENTION

Known examples of antibiotics having a clerodane-type diterpene structure include terpentecin (MF730-N6) produced by a microorganism belonging to the genus Kitasatosporia [refer to EP 205981A; The Journal of Antibiotics, 38, 1664 (1985); and ibid. 38, 1819 (1985)] and clerocidin (PR-1350) produced by a microorganism belonging to the genus Oidiodendron [refer to U.S. Pat. No. 4,576,961; The Journal of Antibiotics, 36, 753 (1983); and Tetrahedron Letters, 25, 465 (1984)].

Both of clerodane-type diterpene antibiotics usually occur as an equilibrium mixture of tautomers which are chemically equivalent with each other. For example, it is known that clerocidin is present in the form of an equilibrium mixture of monomers such as hydroxyaldehyde (compound A) and hemiacetal (compound B) or a dimer (compound C), as shown by the following formulae.

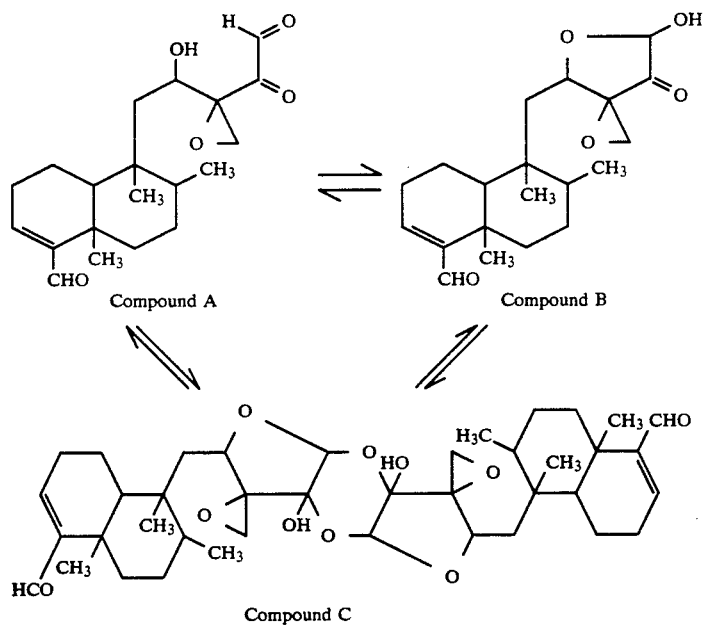

Compound A

Compound B

Compound C

SUMMARY OF THE INVENTION

It is an object of the present invention to provide UCT4-B having antitumor and antibacterial activities as well as a process for producing a clerodane-type diterpene derivative using a microorganism belonging to the genus Streptomyces.

The present invention relates to a process for producing a clerodane-type diterpene derivative represented by formula (I):

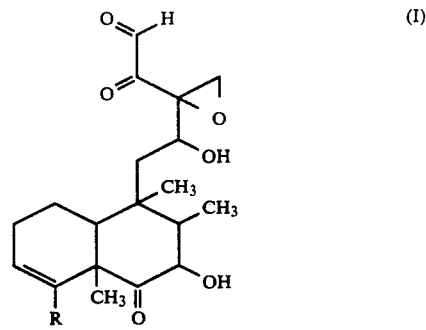

wherein R represents a —CH₃ (terpentecin) or —CH₂OH (UCT4-B); which comprises culturing a microorganism belonging to the genus Streptomyces and capable of producing said clerodane-type diterpene derivative in a medium so as to accumulate said clerodane-type diterpene derivative in the culture and recovering the clerodane-type diterpene derivative from said culture; and UCT4-B represented by formula (II):

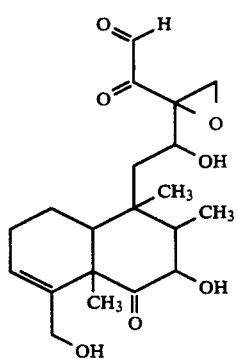

as well as chemically equivalent tautomers thereof.

DETAILED DESCRIPTION OF THE INVENTION

Figure 1:
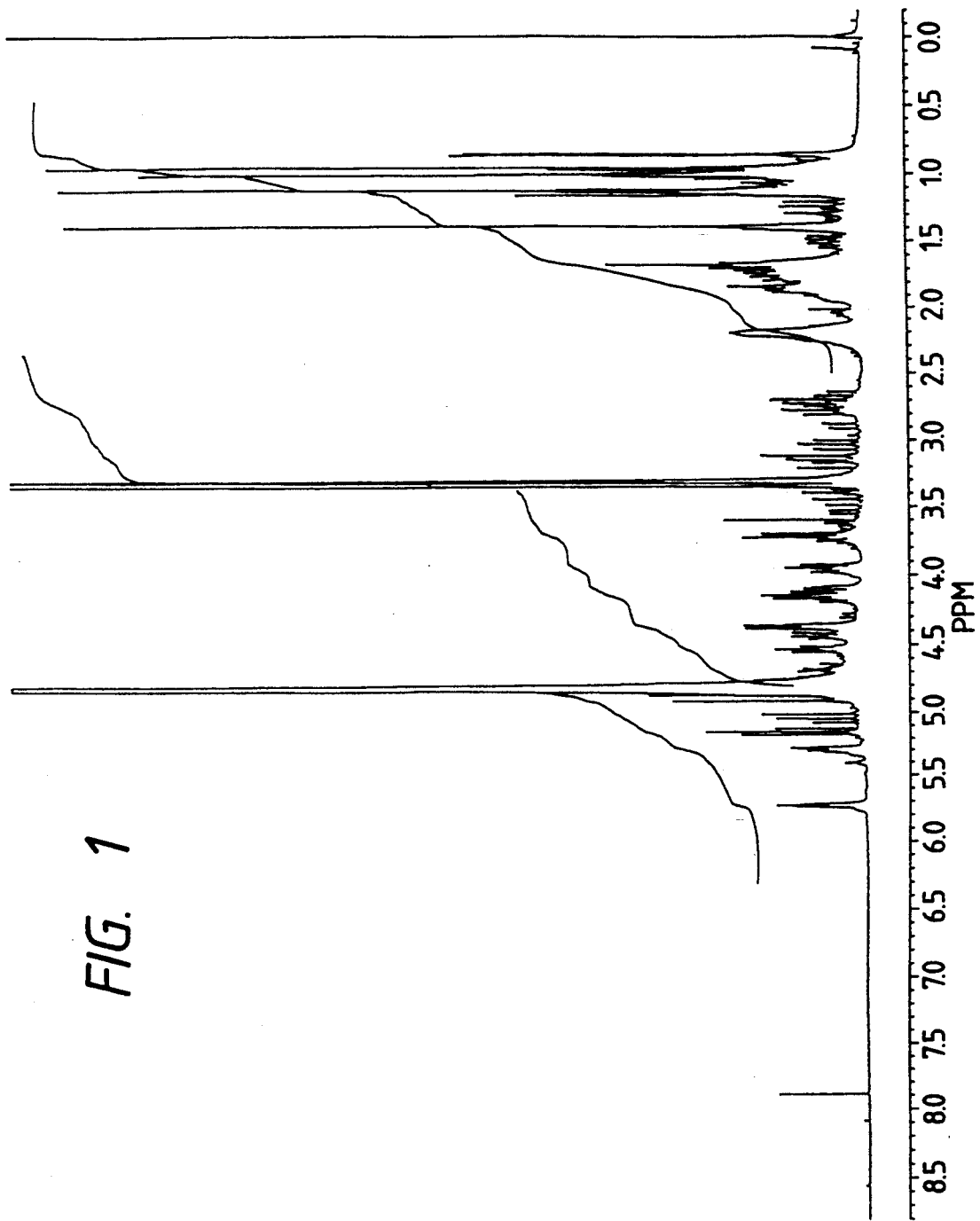
FIG. 1 shows the $^1$H-NMR spectrum of UCT4-B.

Now a process for producing UCT4-B and terpentecin will be described.

UCT4-B and terpentecin can be obtained by culturing a microorganism belonging to the genus Streptomyces and capable of producing UCT4-B and terpentecin so as to accumulate UCT4-B and terpentecin in the culture and recovering the UCT4-B and terpentecin from said culture.

As the UCT4-B and terpentecin-producing strain, any strain may be used so long as it belongs to the genus Streptomyces and can produce UCT4-B and terpentecin. A typical example thereof is strain S-464 which is newly isolated by the present inventors.

The mycological properties of the strain S-464, which will be given hereinbelow, are determined in accordance with a method for determining the properties of Streptomyces strains recommended by the International Streptomyces Project (ISP) [refer to E. B. Shirling and D. Gottlib, Int. J. Syst. Bacteriol., 16, 313 (1966)]. Diaminopimelic acid isomers in the hydrolysate of the whole cells are identified in accordance with the method reported by B. Becker et al. [refer to Appl. Microbiol., 12, 421 (1964)]. An optical microscope is used for morphological studies, while a scanning electron microscope is used, in particular, for observing the morphology of the surface of a spore. Colors are expressed in accordance with Color Harmony Manual, Container Co. of America, 4th ed. (1958).

The mycological properties of the strain S-464 are as follows.

(1) Morphology

Aerial hypha: branched.
Submerged hypha: branched but not fragmented.
Spore: attached to hyphae as a long refractile or loop chain consisting of 10 to 30 or more fragmented spores.
Surface of spore: smooth.
Motility of spore: no.
Shape and size of spore: ellipsoid (0.5×0.7 μm).
Neither any sclerotia nor any sporangiums are observed.

(2) Color

Aerial hypha: white.
Submerged hypha: pale yellow - yellowish brown.
Soluble pigment: pale yellow.
Melanin pigment: yes.

Chemical composition of cell wall

Stereostructure of diaminopimelic acid: LL-type.

(4) Physiological properties

Anabolism of carbon source:
Anabolized carbon source: glucose, xylose, inositol, mannitol, arabinose, rhamnose, raffinose, lactose, sucrose and galactose.
Unanabolized carbon source: salicin.
*Gelatin liquefaction: negative
Starch hydrolysis: positive.
*Skim milk solidification: negative.
*Skim milk peptonization: positive.
*Decomposition of cellulose: positive.
**Growth temperature range: 16°-37° C. (optimum temperature: 28°-32° C.).

Note: *The effects on gelatin, skim milk and cellulose are expressed in the results of a test performed after 1 month at 28° C., while **the growth temperature range is determined based on the results observed 2 days.

(5) Growth in various agar media

The S-464 strain was cultured in various agar media at 28° C. for 28 days. Table 1 shows the results.

In Table 1, G represents the growth level, AM represents the attachment and color of aerial hyphae, SM represents the color of submerged hyphae and P represents the color of a soluble pigment.

TABLE 1

| Medium | Growth |
|---|---|
| Sucrose/nitrate agar medium | G: moderate.<br>AM: poor, white.<br>SM: light ivory (2ca).<br>P: no. |
| Glucose/asparagine agar medium | G: good.<br>AM: rich, light ivory (2ca).<br>SM: light ivory (2ca).<br>P: no. |
| Glycerol/asparagine agar medium | G: good.<br>AM: rich pearl - shell pink (3ba - 5ba).<br>SM: nude tan (4gc).<br>P: yes, pale yellow. |
| Starch agar medium | G: good.<br>AM: rich, natural - white (3dc).<br>SM: apricot (4ge).<br>P: yes, a little. |
| Tyrosine agar medium | G: good.<br>AM: rich, white.<br>SM: nude tan (4gc).<br>P: yes, brown. |
| Nutrient agar medium | G: good.<br>AM: rich, natural (3dc).<br>SM: toast tan - nude tan (4lg - 4gc).<br>P: yes, pale yellow. |
| Yeast/malt agar medium | G: good.<br>AM: rich, sand (3cb).<br>SM: light brown (4ng).<br>P: yes, pale yellow. |
| Oatmeal agar medium | G: good.<br>AM: no.<br>SM: dark brown (4pn).<br>P: yes, brown. |
| Peptone/yeast extract/iron agar medium | G: moderate.<br>AM: no.<br>SM: beaver (4li).<br>P: yes, brown. |

(6) Identification of strain S-464

Since LL-form diaminopimelic acid is detected from the strain S-464, it falls within Actinomycetes of the cell wall I type [refer to Int. J. Syst. Bacteriol., 20, 435 (1970)]. Further, the above-mentioned morphological characteristics of this strain suggest that it reasonably belongs to the genus Streptomyces.

The species of this strain S-464 has been identified, from among those belonging to the genus Streptomyces, by detecting species whose characteristics are similar to those of this strain (namely, white hyphae, refractile or loop spore chain, smooth spore surface, production of the melanin-like pigment, production of the soluble pigment and metabolism pattern of carbon sources) from species recited in Approved Lists of Bacterial Names in view of the description of ISP [Int. J. Syst. Bacteriol., 18, 69 (1968); ibid., 18, 279 (1968); ibid., 19, 391 (1969); and ibid., 22, 265 (1972)] and Bergey's Manual of Determinative Bacteriology [ed. by R. E. Buchanan and N. E. Gibbons, 8th ed., Williams and Wilkins Co., (1974)].

Thus it has been identified that the strain S-464 belongs to a novel species of the genus Streptomyces. This strain was deposited with the Fermentation Research Institute (FRI), Agency of Industrial Science and Technology of 1-3, Higashi 1-chome, Tsukuba-shi, Ibaraki, Japan as Streptomyces sp. S-464 No. FERM BP-3036 on Jul. 31, 1990 under the Budapest treaty.

The strain S-464 may be cultured in accordance with a method commonly employed for culturing Actinomycetes. Either a synthetic medium or a natural one may be used so long as it contains a carbon source, a nitrogen source and inorganic matters, which can be metabolized by this strain, substances required for the growth thereof and substances capable of promoting the production of the target compounds.

Examples of the carbon source include glucose, starch, dextrin, mannose, fructose, sucrose, lactose, xylose, arabinose, mannitol, molasses and mixtures thereof. Further, hydrocarbons, alcohols and organic acids may be used depending on the metabolism capability of the strain. Examples of the nitrogen source include ammonium chloride, ammonium sulfate, ammonium nitrate, sodium nitrate, urea, peptone, meat extract, yeast extract, dry yeast, corn steep liquor, soybean flour, casamino acids and mixtures thereof. Further, inorganic salts such as sodium chloride, potassium chloride, magnesium sulfate, calcium carbonate, potassium dihydrogen phosphate, dipbtassium hydrogen phosphate, ferrous sulfate, calcium chloride, manganese sulfate, zinc sulfate and copper sulfate may be added to the medium, if required. Furthermore, trace components capable of promoting the growth of the strain and the production of UCT4-B and terpentecin may be optionally added thereto.

It is preferable to culture this strain by the liquid culture method, in particular, the submerged agitation culture method. The culture temperature ranges from 16° to 37° C., preferably from 25° to 32° C., and the pH value of the medium is maintained at 4 to 10, preferably 6 to 8, during the culture period by adding, for example, sulfuric acid, aqueous ammonia or an ammonium carbonate solution.

When the strain is cultured by the liquid culture method for 1 to 7 days, UCT4-B and terpentecin are generally produced and accumulated in the culture medium and cells. When the production in the culture medium reaches the maximum level, the culture is ceased.

The UCT4-B and terpentecin may be isolated from the culture medium and purified by a method commonly employed for isolating and purifying metabolites of a microorganism from its culture.

For example, the culture medium is filtered and thus separated into a culture filtrate and cells. Next, the cells are extracted with, for example, chloroform or acetone. Then the extract is combined with the culture filtrate and passed through a column packed with a polystyrene adsorbent such as Diaion HP20 (product of Mitsubishi Kasei Corporation) to thereby adsorb the active components contained therein, followed by eluting with, for example, ethyl acetate or acetone. The obtained eluate is concentrated and purified by chromatography commonly employed in the art, for example, silica gel column chromatography or high-performance liquid chromatography. Thus UCT4-B and terpentecin can be obtained as a white powder.

The UCT4-B thus obtained may be in the form of, for example, an equilibrium mixture of chemically equivalent tautomers represented by the following formulae. All the isomers including these tautomers are involved in the present invention.

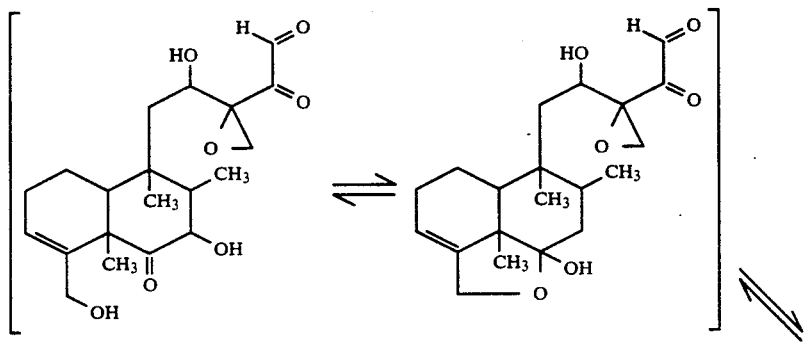

-continued

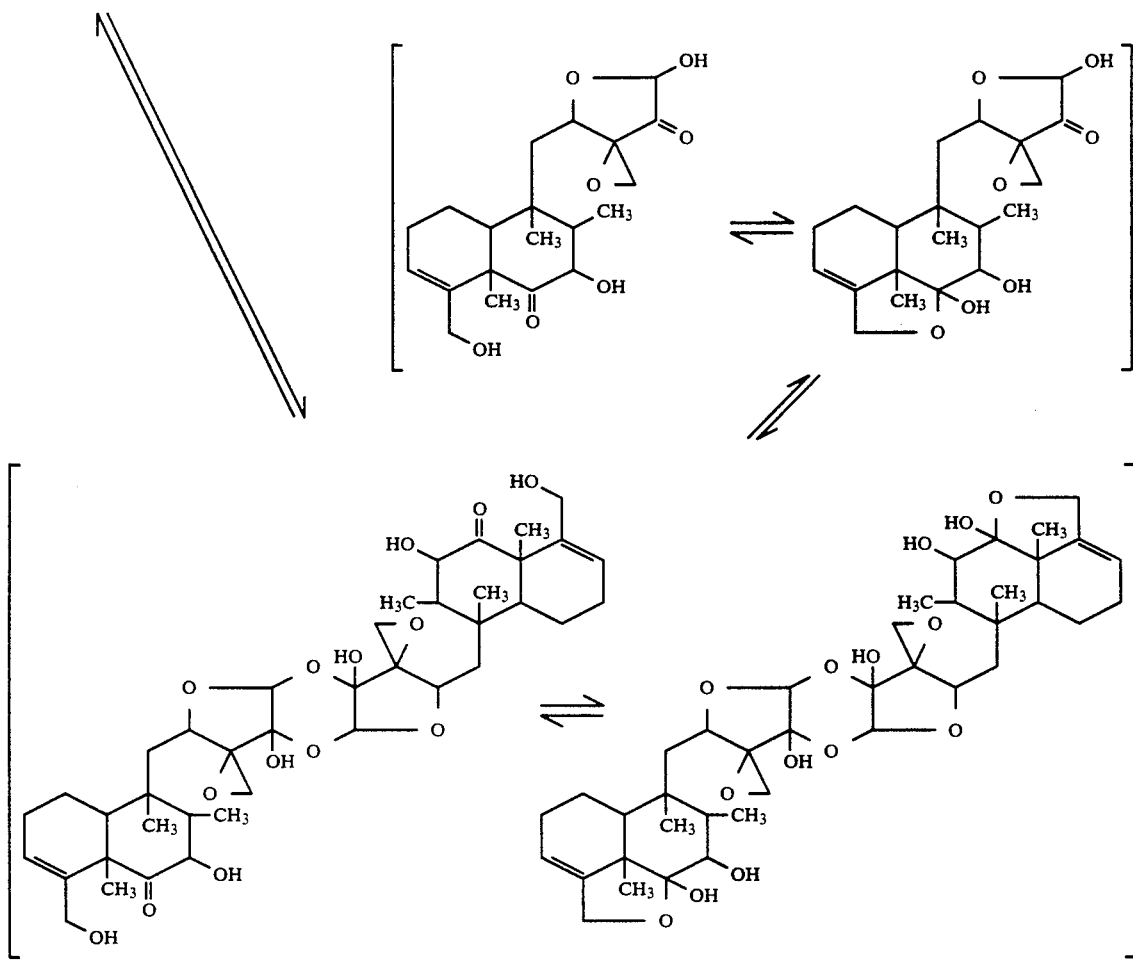

As the following reaction scheme shows, an equilibrium mixture of the compounds 2 and 3 each having a quinoxaline ring may be obtained by reacting UCT4-B with o-phenylenediamine. Then the equilibrium mixture is acetylated to thereby give a single compound 4 which is never contaminated with any equilibrium mixture of tautomers (refer to Reference Examples 1 and 2).

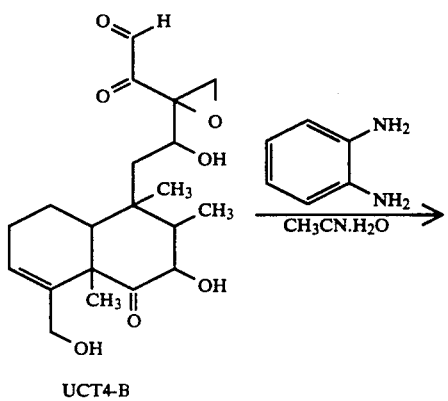

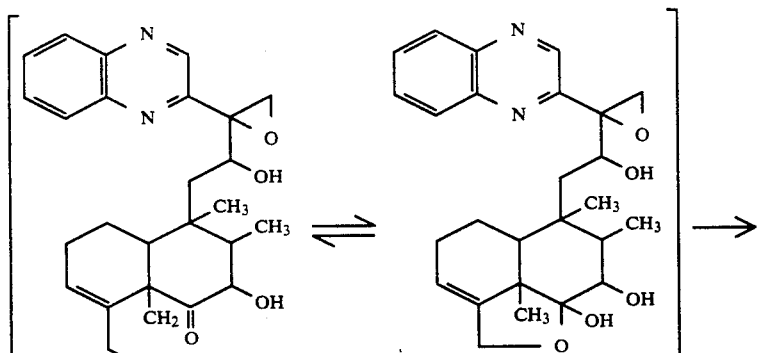

Compound 2    Compound 3

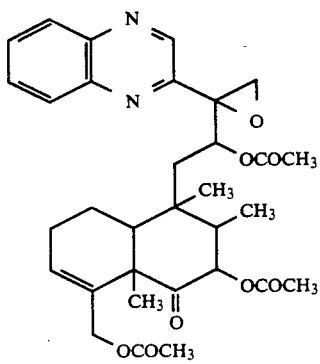

Compound 4

Thus the structure of UCT4-B has been more clearly confirmed.

Now the biological activities of UCT4-B will be illustrated by reference to the following Test Examples.

TEST EXAMPLE 1

Antibacterial Activity

The antibacterial activities of UCT4-B on four bacteria (i.e., *Staphylococcus aureus, Enterococcus faecium, Bacillus subtilis, Klebsiella pneumoniae*) were examined by the agar dilution method (pH 7.0) [refer to "Biseibutsu Jikken Manyuaru (Manual of The Microbial Experiments)" 80, Kodansha (1986)].

The results are shown in terms of the minimum growth inhibition concentration (MIC) in Table 2.

TABLE 2

| Test strain | MIC (μg/ml) of UCT4-B |
| --- | --- |
| *Staphylococcus aureus* ATCC 6538P | 4.1 |
| *Enterococcus faecium* ATCC 10541 | 4.1 |
| *Bacillus subtilis* ATCC 10707 | 8.3 |
| *Klebsiella pneumoniae* ATCC 10031 | 2.1 |

TEST EXAMPLE 2

Acute Toxicity

UCT4-B was intravenously administered once to ddy mice weighing about 20 g (each group having 5 animals) and then the survival state of the animals was monitored for 14 days following the administration. Then $LD_{50}$ of the compound was calculated based on the mortality of mice in each group in accordance with the Behrens-Kärber method. As a result, it was found that the $LD_{50}$ of UCT4-B is 50 mg/kg or above.

TEST EXAMPLE 3

Effect on Lymphocytic Leukemia $1 \times 10^6$ lymphocytic leukemia p338 tumor cells were intraperitoneally transplanted into CDF male mice weighing 22 g (each group having 5 animals). 24 hours after the transplantation, 0.2 ml of a solution of UCT4-B in physiological saline or 0.2 ml of physiological saline (the control group) was intraperitoneally administered to the animals.

The results of the test are expressed in terms of T/C (%) calculated by dividing the average survival days of each test group (T) with that of the control group (C). Table 3 shows the results.

TABLE 3

| Test compound | Dose (mg/kg) | Life-prolonging effect (T/C %) |
| --- | --- | --- |
| UCT4-B | 50 | 141 |
|  | 25 | 137 |
|  | 12 | 127 |
|  | 6 | 131 |
|  | 3 | 124 |

To further illustrate the embodiments of the present invention, the following Examples and Reference Examples will be given.

EXAMPLE 1

Streptomyces sp. S-464 was inoculated into 300 ml of a seed medium (pH 7.2 before sterilization) comprising 5 g/l of Bacto Tripton (product of Difco), 5 gl of yeast extract, 3 g/l of meat extract, 10 g/l of soluble starch, 10 g/l of glucose and 5 g/l of calcium carbonate contained in a 2 l Erlenmeyer flask and cultured at 30° C. under shaking at 200 rpm for 48 hours.

The seed culture thus obtained was then transferred into 100 l of a fermentation medium of the following composition in a 200 l culture tank at a ratio of 10% by volume and cultured at 28° C. under aerating at a ratio of 15 /min. and agitating at 200 rpm.

Composition of the fermentation medium: 5% of soluble starch, 3% of $KNO_3$, 0.5 g/l of $KH_2PO_4$, 0.5 g/l of $MgSO_4.7H_2O$ and 5 g/l of calcium carbonate (the pH value of the above medium had been adjusted to 7.0 with NaOH prior to the sterilization).

Then the culture was continued for 67 hours while controlling the pH value of the medium to 7 with 4N $H_2SO_4$. Next, the cells and precipitate were removed from the culture medium by filtration and thus 100 l of a filtrate was obtained. The filtrate was concentrated, diluted with water and then passed through a column packed with a polystyrene adsorbent Diaion HP20 (10 l) to thereby adsorb the active substances.

After eluting impurities with deionized water and 50 methanol, UCT4-B was eluted with 60% methanol and then terpentecin was eluted with 80% methanol.

The 60% methanol fraction containing UCT4-B was concentrated and adjusted to pH 4. Then the active substance was extracted with ethyl acetate. The ethyl acetate layer was concentrated and passed through a column packed with silica gel (Lichroprepsi 60, product of Merck Inc.) so as to adsorb the active substance. Next, the adsorbed substance was eluted with chloroform, chloroform/methanol (100:1 by volume) and chloroform/methanol (50:1 by volume) under elevated pressure to approximately 10 kg/cm$^2$. The obtained fraction was subjected to column chromatography with the use of Sephadex LH20 and eluted with methanol to thereby give an active fraction. This fraction was then purified with reverse-phase high performance liquid chromatography [column: YMC-Pack (YMC Ltd.), ODS SH363-5; development solvent: $CH_3OH$ 0.7 l+$H_2O$ 0.03 l; flow rate: 20 ml/min.; detection: UV absorption at 230 nm]. The active fraction thus obtained was concentrated to dryness to give 100 mg of UCT4-B as a white powder.

The physiochemical properties of the obtained UCT4-B are as follows.

As described above, it is assumed that UCT4-B is in the form of an equilibrium mixture of tautomers, similar to terpentecin and clerocidin. Therefore its physiochemical properties might vary depending on the determination conditions and the method for preparing the sample. Thus the physicochemical properties of the sample prepared by the method described in the above Example will are given below. The instruments employed for the determination are as follows.

m.p.: Micro Melting Point Meter produced by Yanagimoto Seisakusho, K.K.

Optical rotation: Polarimeter DIP-370 produced by Nippon Bunko Kogyo K.K.

Mass spectrum: M-80B produced by Hitachi, Ltd.

UV absorption spectrum: Spectrophotometer 200-20 produced by Hitachi, Ltd.

IR absorption spectrum: JIR-RFX 3001 produced by JEOL Ltd. or IR-810 produced by Nippon Bunko Kogyo K.K.

$^1H$ and $^{13}C$-NMR spectra: AM500 or AM400 produced by Bruker Co.

A) Form: colorless powder.

B) m.p.: within a range of from 160° to 172° C.

C) Optical rotation:
In a chloroform solution, $[\alpha]_D^{27} = +27.8°$ (c=0.53). When dissolved in a 50% aqueous acetonitrile solution, $[\alpha]_D^{27} = +23.2°$ (c=0.53) immediately after the dissolution. 195 minutes after the dissolution, $[\alpha]_D^{27} = +1.21°$ (c=0.53) and then this level was maintained.

D) EI mass spectrum: m/z 380, 365, 249, 219, 203, 165, 135, 125, 109, 107 and 105.

E) Secondary ion mass spectrum: (methanol solution, matrix: glycerol) m/z 743, 725, 491, 473, 455, 437, 381, 363, 345, 317, 259, 237, 225, 215 and 201.

F) UV absorption spectrum: (acetonitrile solution) nothing but the terminal absorption was observed.

G) IR absorption spectrum: (KBr method) 3431, 2966, 1707, 1385, 1016 and 999 cm$^{-1}$.

(H) Solubility: highly soluble in methanol, chloroform and ethyl acetate, soluble in water and acetonitrile and insoluble in hexane.

I) $^1H$-NMR spectrum: (500 MHz, $CD_3OD$ solution) shown in FIG. 1.

Figure 2:
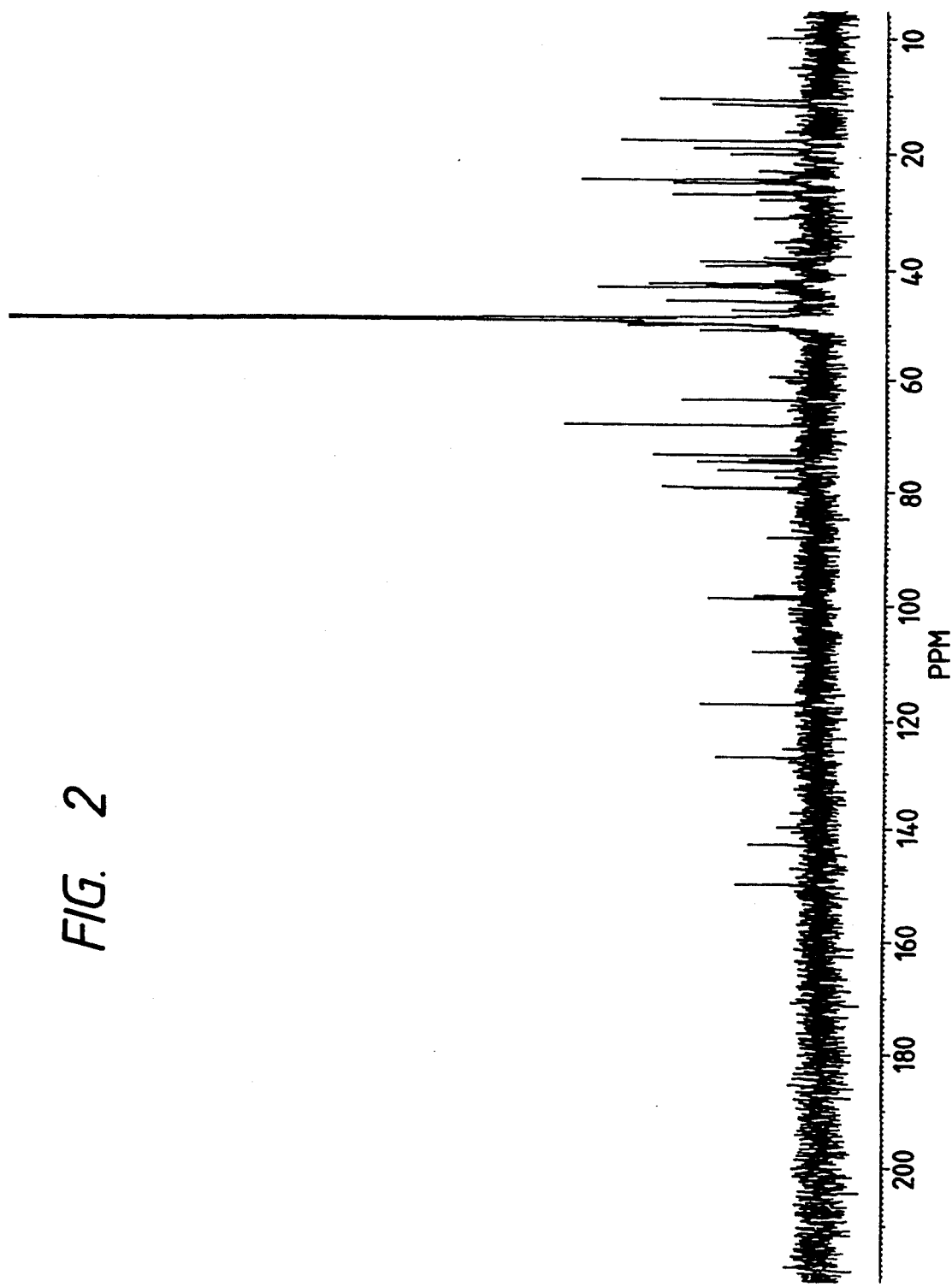
FIG. 2 shows the $^{13}$C-NMR spectrum of UCT4-B.

J) $^{13}C$-NMR spectrum: (125 MHz, $CD_3OD$ solution) shown in FIG. 2.

K) Coloration: positive in coloration reactions of anisaldehyde, sulfuric acid, iodine and phosphomolybdic acid and negative in Dragendorff's reaction.

On the other hand, the 80% methanol fraction containing terpentecin was concentrated and purified in the same manner as the one employed for purifying UCT4-B. Thus 90 mg of terpentecin was obtained.

The $^1H$-NMR spectrum and IR spectrum of the terpentecin thus obtained agreed with the reported ones [refer to The Journal of Antibiotics, 38, 1819 (1985)].

REFERENCE EXAMPLE 1

Preparation of o-phenylenediamine Adducts of UCT4-B (compounds 2 and 3)

13.4 mg of UCT4-B was dissolved in 1 ml of 50% aqueous acetonitrile and 8.3 mg of o-phenylenediamine was added thereto. The mixture was stirred at room temperature for 1 hour. Then the reaction mixture was concentrated under reduced pressure. The crude product thus obtained was purified by preparative thin layer chromatography [product of Merck Inc., Kieselguhr 60F$_{254}$ Art 5744; development solvent: chloroform:methanol (9:1 by volume)]. Thus 5.2 mg of an equilibrium mixture of the compounds 2 and 3 (1:1) which could not be separated by TLC or HPLC was obtained. Physicochemical data of the equilibrium mixture of the compounds 2 and 3:

Rf: 0.70 [product of Merck Inc., Kieselguhr 60F$_{254}$ Art 5719; development solvent: chloroform:methanol (9:1 by volume)].

0.44 [product of Merck Inc., HPTLC CNF$_{254}$S Art 16464; development solvent: acetonitrile:water (1:1 by volume)].

High resolution EI mass spectrum: m/z as $C_{26}H_{32}O_5N_2$: found: 452.2298 (M+). calculated: 452.2308.

EI mass spectrum: m/z 452 (M+), 434, 201, 185, 173, 157, 144, 129 and 102.

IR absorption spectrum: (KBr method) 3425, 2960, 2924, 1385, 1049, 1014 and 763 cm$^{-1}$.

$^1H$-NMR spectrum: (500 MHz, $CDCl_3$ solution) δppm.

Compound 2

8.81 (1H, s), 8.15 (1H, m), 8.01 (1H, m), 7.81 (2H, m), 5.73 (1H, m), 4.48 (1H, m), 4.30 (1H, d, J=7.5 Hz), 4.29–4.20 (2H, m), 3.59 (1H, br. s, disappeared when D$_2$O was added), 3.42 (1H, d, J=4.6 Hz), 3.13 (1H, d, J=4.6 Hz), 2.98 (1H, br. d, J=11.1 Hz), 2.35–2.20 (2H, m), 1.96 (1H, d, J=15.3 Hz), 1.92 (2H, m), 1.76 (1H, m), 1.70 (1H, m), 1.48 (3H, s), 1.09 (3H, d, J=7.1 Hz) and 1.03 (3H, s).

Compound 3

8.79 (1H, s), 8.12 (1H, m), 8.06 (1H, m), 7.80 (2H, m), 5.33 (1H, m), 4,46 (1H, m), 4.13 (1H, m), 4.08 (1H, d, J=11.0 Hz), 3.89 (1H, d, J=12.1 Hz), 3.36 (1H, d, J=4.8 Hz), 3.08 (1H, d, J=4.8 Hz), 2.88 (1H, br. s, disappeared when D$_2$O was added), 2.35–2.20 (2H, m), 2.15 (1H, dd, J=9.1, 7.4 Hz), 1.85 (1H, m), 1.84 (2H, m), 1.77 (1H, dq, J=12.1, 7.3 Hz), 1.58 (1H, dd, J=15.0., 9.4 Hz), 1.17 (3H, s), 0.99 (3H, s) and 0.88 (3H, d, J=7.3 Hz).

REFERENCE EXAMPLE 2

Preparation of Acetylated o-phenylenediamine Adduct of UCT4-B

Compound 4

0.5 ml of pyridine and 0.5 ml of acetic anhydride were added to 2.4 mg of an equilibrium mixture (1:1) of the compounds 2 and 3 and stirred at room temperature for 15 hours. The reaction mixture was concentrated and the crude product thus obtained was purified by preparative thin layer chromatography [product of Merck Inc., Kieselguhr 60F$_{254}$ Art development solvent:hexane:ethyl acetate (1:1 by volume)]. Thus 1.9 mg of a single acetylated product (compound 4) was obtained.

Physicochemical Data of the Compound 4

Rf: 0.41 [product of Merck Inc., Kieselguhr 60F$_{254}$ Art 5719; development solvent: hexane:ethyl acetate (1:1 by volume)].

0.60 [product of Merck Inc., development solvent: chloroform:methanol (98:2 by volume)].

High resolution EI mass spectrum: m/z as C$_{32}$H$_{38}$O$_8$N$_2$: found: 578.2614 (M+). calculated: 578.2625.

EI mass spectrum: m/z 578 (M+), 536, 518, 494, 476, 460, 260, 235 and 207.

IR absorption spectrum: (KBr method) 2925, 1747, 1373, 1232, 1053, 1026 and 768 cm$^{-1}$.

$^1$H-NMR spectrum: (500 MHz, CDCl$_3$ solution) δppm. 8.76 (1H, m), 8.09 (1H, m), 8.02 (1H, m), 7.77 (2H, m), 5.88 (1H, d, J=10.2 Hz), 5.75 (1H, m), 5.51 (1H, m), 4.87 (1H, dd, J=12.7, 1.0 Hz), 4.66 (1H, dd, J=12.7, 0.7 Hz), 3.30 (1H, d, J=5.0 Hz), 3.10 (1H, d, J=5.0 Hz), 2.91 (1H, dd, J=10.5, 3.6 Hz), 2.58 (1H, d, J=15.1 Hz), 2.19 (2H, m), 2.15 (1H, dq, J=13.8, 6.9 Hz), 2.13 (3H, s), 2.12 (3H, s), 2.06 (3H, s), 1.79 (1H, dd, J=15.1, 10.2 Hz), 1.49 (3H, s), 1.16 (3H, s) and 1.01 (3), d, J=6.9 Hz).

What is claimed is:

1. A compound represented by formula (II):

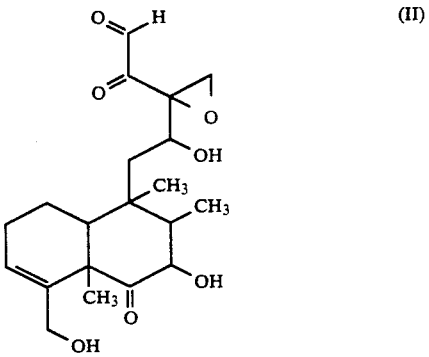

(II)

and chemically equivalent tautomers thereof.

* * * * *